(12) United States Patent
Su et al.

(10) Patent No.: US 7,763,169 B2
(45) Date of Patent: Jul. 27, 2010

(54) MAGNETIC SEPARATION DEVICE

(75) Inventors: Chih-Hsien Su, Kaohsiung (TW); Chao-Hung Kao, Taipei (TW); Yuh-Jiuan Lin, Taipei (TW)

(73) Assignee: Industrial Technology Research Institute, Hsin-Chu (TW)

( * ) Notice: Subject to any disclaimer, the term of this patent is extended or adjusted under 35 U.S.C. 154(b) by 444 days.

(21) Appl. No.: 12/014,708

(22) Filed: Jan. 15, 2008

(65) Prior Publication Data
US 2009/0028758 A1    Jan. 29, 2009

(30) Foreign Application Priority Data
Jul. 26, 2007    (TW) .................................. 96127235

(51) Int. Cl.
*B03C 1/02* (2006.01)
(52) U.S. Cl. ........................... 210/223; 422/50; 422/58; 422/68.1; 422/100; 422/101; 422/102; 422/104; 436/174; 436/177; 436/178; 436/526; 210/222; 210/294; 209/217
(58) Field of Classification Search .................. 422/50, 422/58, 68.1, 100–102, 104; 436/149, 174, 436/177, 178, 526; 210/222, 223, 294; 209/217
See application file for complete search history.

(56) References Cited
U.S. PATENT DOCUMENTS

| 5,571,481 | A |  | 11/1996 | Powell et al. |  |
|---|---|---|---|---|---|
| 5,647,994 | A |  | 7/1997 | Tuunanen et al. |  |
| 5,705,062 | A | * | 1/1998 | Knobel | 210/205 |
| 6,187,270 | B1 | * | 2/2001 | Schmitt et al. | 422/101 |
| 6,455,325 | B1 | * | 9/2002 | Tajima | 436/526 |
| 6,468,810 | B1 |  | 10/2002 | Korpela |  |
| 7,226,537 | B2 | * | 6/2007 | Broyer et al. | 210/222 |

FOREIGN PATENT DOCUMENTS

| CN | 1580775 | 2/2005 |
|---|---|---|
| TW | I251841 | 3/2006 |
| TW | I294039 | 3/2008 |

* cited by examiner

*Primary Examiner*—Jill Warden
*Assistant Examiner*—Dean Kwak
(74) *Attorney, Agent, or Firm*—WPAT, PC; Justin King

(57) ABSTRACT

A magnetic separation device, comprising: a separator, including a top base and a bottom base; at least a groove set, each composed of two arc-like grooves having curvatures opposite to each other; at least a magnetic member, being movably fitted inside the two arc-like grooves of the at least one groove set; and at least a test tube slot, each being formed at the outer rim of a base selected from the group consisting of the top and the bottom base of the separator; wherein the top and the bottom bases are assembled by means of a pivotal axis piecing through about at the center of the top and the bottom bases for enabling the two bases to rotate relative to each other; and one of the two arc-like groove is formed on the top base at a surface thereof facing toward the bottom base while forming another arc-like groove on the bottom base at a surface thereof facing toward the top base. With the aforesaid device, the magnetic member can be driven to slide inside the groove set while the top and the bottom bases are driven to rotate relative to each other, thereby, the magnetic member can be moved between two positions whereas one is near the test tube slot and the other is away from the same.

14 Claims, 5 Drawing Sheets

MAGNETIC SEPARATION DEVICE

CROSS-REFERENCE TO RELATED APPLICATION

The application claim the priority benefit of Taiwan patent application serial no. 96127235, filed on Jul. 26, 2007.

FIELD OF THE INVENTION

The present invention relates to a magnetic separation device, and more particularly, to a device for separating magnetic particles which utilizes the rotation of a rotary mechanism to alter the relative position between a magnet and a sample cell so as to separate a trace amount of an entity of interest from a complicated mixture for purification.

BACKGROUND OF THE INVENTION

Magnetic separation device, adapted for magnetic particle purification and/or separation, can effectively separate a trace amount of an entity of interest from a compound or mixture for obtaining such entity with high purity. However, in a conventional magnetic separation process, usually a number of washing cycles are carried out after magnetic particles are separated and the unwanted liquid phases are removed, each including repetitive elution and aspiration processes. Owing to the performing of such washing cycles usually requires the test tubes to be taken out of the magnetic separation device, splashing of the contents will occur, possibly causing cross-contamination between test tubes or contamination of an operator, not to mention that it is time-consuming and inconvenient when there are a plenty of test tubes required to be taken out.

There are known two types of magnetic separation device. One of which is shaped like a rod, a pen or a pipette such as those disclosed in U.S. Pat. No. 6,468,810, entitled "Magnetic particle transfer device and method", U.S. Pat. No. 5,647,994, entitled "Method and apparatus for separating magnetic particles from a solution", and U.S. Pat. No. 6,455,325, entitled "Liquid processing method making use of pipette device and apparatus for same". The aforesaid devices usually immerse a magnetic probe directly into a solution for attracting magnetic particles along with targeted bio-substances attached thereupon. Nevertheless, they are disadvantageous in that: the magnetic portion of the probe must be covered by disposable protective membrane, that although cross-contamination between solutions of different test tubes can be prevented, it is troublesome to operate. Moreover, as the separation of magnetic particle in such devices require the probe to contact with the solution directly, the purification efficiency can easily be adversely affected when the probe is contaminated and adhered by some nonspecific impurities which also might cause some damage to the intended targeted bio-substances.

Another type of magnetic separation device uses magnetic members to apply magnetic forces on solution-containing test tubes from the outside thereof, such as a magnetic capture rack with slidable magnetic member disclosed in U.S. Pat. No. 5,571,481, by which the contamination caused by the direct contact of the probe can be prevented. The aforesaid magnetic capture rack is composed of a housing member having a plurality of sample cells disposed as a linear array, and a slidable and detachable magnetic member. By driving the magnetic member to move in parallel to the linear array of the plural sample cells in a reciprocating manner, magnetic force of the magnetic member can be applied to or removed from the test tubes received in the sample cells according to the reciprocating movement, and thereby, trace entity of interest can be separated from mixtures in the test tubes. It is noted that there must be enough space structured inside the magnetic capture rack for housing the housing member and the magnetic member, and also for enabling the magnetic member to move in such reciprocating manner without being obstructed.

Another non-contact magnetic separation device is the one disclosed in U.S. Pat. No. 5,705,062, entitled "Analytical device for separating magnetic micro-particles from suspensions". The aforesaid analytical device comprises: a disc-shape holder having a circular groove formed thereon; a magnet set, including a pair of magnets, both disposed on the holder and each magnet in the pair being diametrically opposite to the other magnet in the pair and arranged so that the circular groove is sandwiched between the two magnets. In addition, a rotor magazine, arranged above the holder, is configured with at least a sample cell, each capable of holding and positioning a reaction vessel right on top of the circular groove while being received between the two magnets, by which when the rotor magazine is driven to rotate, the reaction vessels lodged in the sample cells will be driven to move along the circular groove and thus pass the magnetic set at each rotation so that entities of interest can be separate from a mixture containing in the reaction vessel. Nevertheless, an additional driving device is required for driving the rotor magazine to rotate while maintaining the reaction vessel to be positioned and received between the pair of magnets of the magnetic set. As the pair of magnets are diametrically opposite relative to the reaction vessel, and the polar axes of the magnets and the longitudinal axis of the reaction vessel include an acute angle, the holder must be large enough for accommodating the magnetic set as well as for configuring the circular groove thereon that is larger enough for the reaction vessel to pass through.

SUMMARY OF THE INVENTION

The object of the present invention is to a magnetic separation device capable of altering magnetic strength at will at any time according to specific requirements of a magnetic separation process without having the test tubes used in the device to be taken out repetitively, by which not only the processing time can be greatly reduced, but also the splashing of the content and cross-contamination can be prevented.

To achieve the above object, the present invention provides a magnetic separation device, comprising: a separator, including a top base and a bottom base; at least a groove set, each composed of two arc-like grooves having curvatures opposite to each other and arranged in a manner that one of the two arc-like groove is formed on the top base at a surface thereof facing toward the bottom base while forming another arc-like groove on the bottom base at a surface thereof facing toward the top base; at least a magnetic member, being movably fitted inside the two arc-like grooves of the at least one groove set; and at least a test tube slot, each being formed at the outer rim of a base selected from the group consisting of the top and the bottom base of the separator to be used for fitting a test tube therein; wherein the top and the bottom bases are assembled by means of a pivotal axis piecing through about at the center of the top and the bottom bases for enabling the two bases to rotate relative to each other; and the magnetic member is driven to slide inside the groove set while the top and the bottom bases are driven to rotate relative to each other, thereby, the magnetic member is moved between two positions whereas one is near the at least one test tube slot and the other is away from the at least one test tube slot.

In an exemplary embodiment of the invention, the two arc-like grooves of the groove set are respectively: an upper groove, formed at the bottom of the top base and curvedly extending from the pivotal axis toward the outer rim of the top base in a radial and centrifugal manner; and a lower groove, formed at the top of the bottom base and curvedly extending from the pivotal axis toward the outer rim of the bottom base in a radial and centrifugal manner; whereby the upper groove intersects with the lower groove when the top base and the bottom base are driven to rotate relative to each other.

In an exemplary embodiment of the invention, the upper and the lower grooves are extending parallel to a plane defined by a Cartesian coordinate system of X- and Y-axes for enabling the magnetic member to move with two degree-of-freedom capability; wherein the plane defined by the Cartesian coordinate system of X- and Y-axes is the datum water level.

In an exemplary embodiment of the invention, the upper and the lower grooves are extending in a space defined by a Cartesian coordinate system of X-, Y-, and Z-axes for enabling the magnetic member to move with three degree-of-freedom capability.

In an exemplary embodiment of the invention, the groove-bottoms of the upper and the lower grooves are curve planes governed by a same curvature while enabling the cross profiles of the two grooves to descend from the pivotal axis to the outer rim of the separator.

In an exemplary embodiment of the invention, the groove-bottoms of the upper and the lower grooves are curve planes governed by a same curvature while enabling the cross profiles of the two grooves to rise from the pivotal axis to the outer rim of the separator.

In an exemplary embodiment of the invention, both the top base and the bottom base are shaped like a round disc while the centers of the two disc-like bases are bored for lodging the pivotal axis.

In an exemplary embodiment of the invention, an axial through hole is formed at the center of the top base; and the pivotal axis is disposed at the center of the bottom base while axially extending into the axial through hole of the top base for pivotally coupling the top and the bottom bases.

In an exemplary embodiment of the invention, the top of the axial through hole formed in the top base is configured with a bearing for coupling to the top of the pivotal axis.

In an exemplary embodiment of the invention, each test tube slot is a through hole boring from the top to the bottom of the base where it is disposed and the axial direction of the through hole is parallel to the axial direction of the pivotal axis.

In an exemplary embodiment of the invention, each through hole is formed at the outer rim of the base where it is disposed as an open slot, in which at least a pin clip is arranged at the wall of the open slot for enabling the open slot to open/close with elasticity and holding a test tube.

In an exemplary embodiment of the invention, a plurality of bulging bar-like elements are attached to the outer wall of the separator for providing friction to allow for holding/rotating the separator by a user.

In an exemplary embodiment of the invention, an anti-slip pad is arranged at the bottom of the separator for providing friction between the separator and the surface where the separator is placed.

In an exemplary embodiment of the invention, the magnetic member is an element selected from the group consisting of magnets, electromagnets or the combination thereof.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
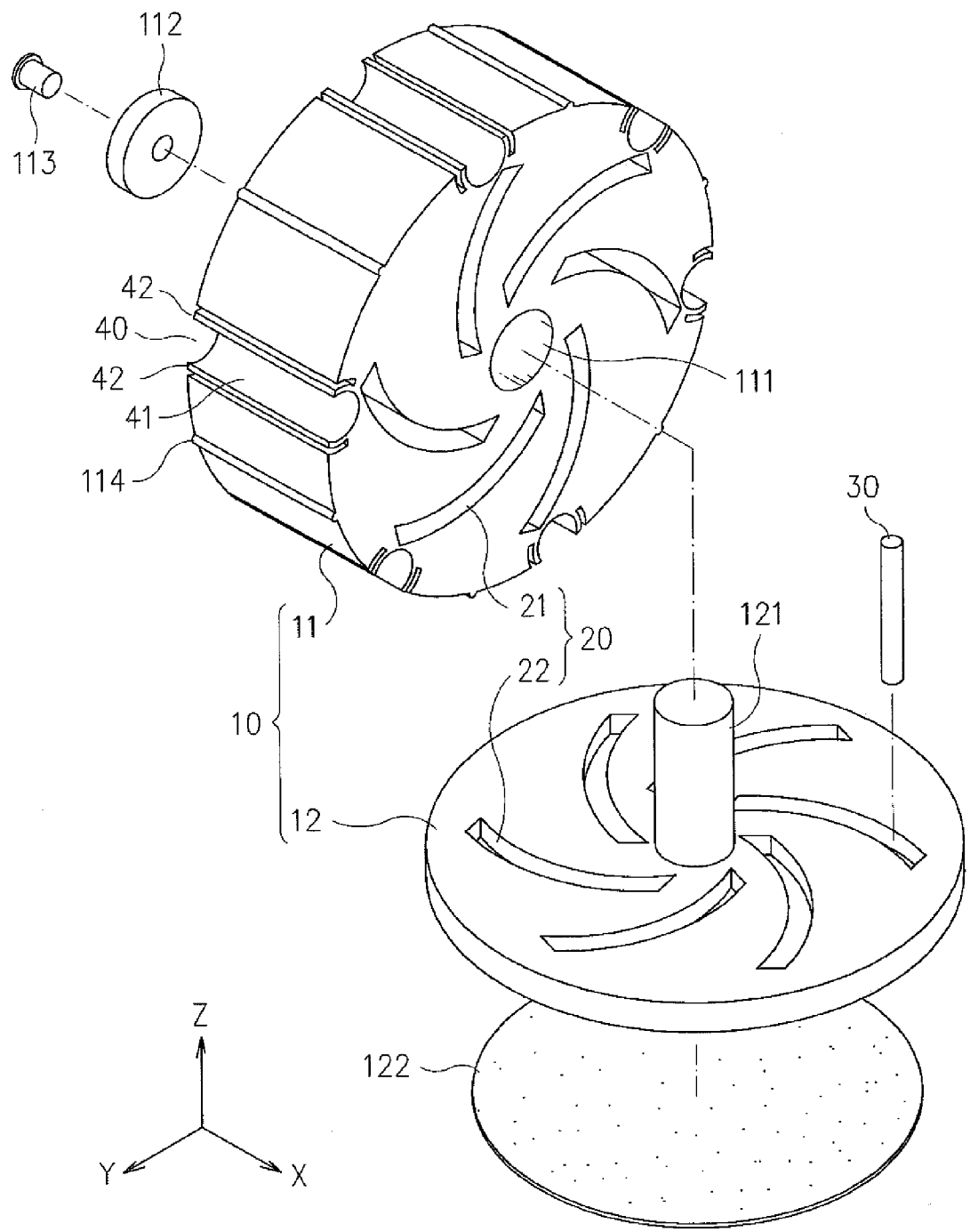
FIG. 1 is an exploded view of a magnetic separation device according to an exemplary embodiment of the invention.
Figure 2:
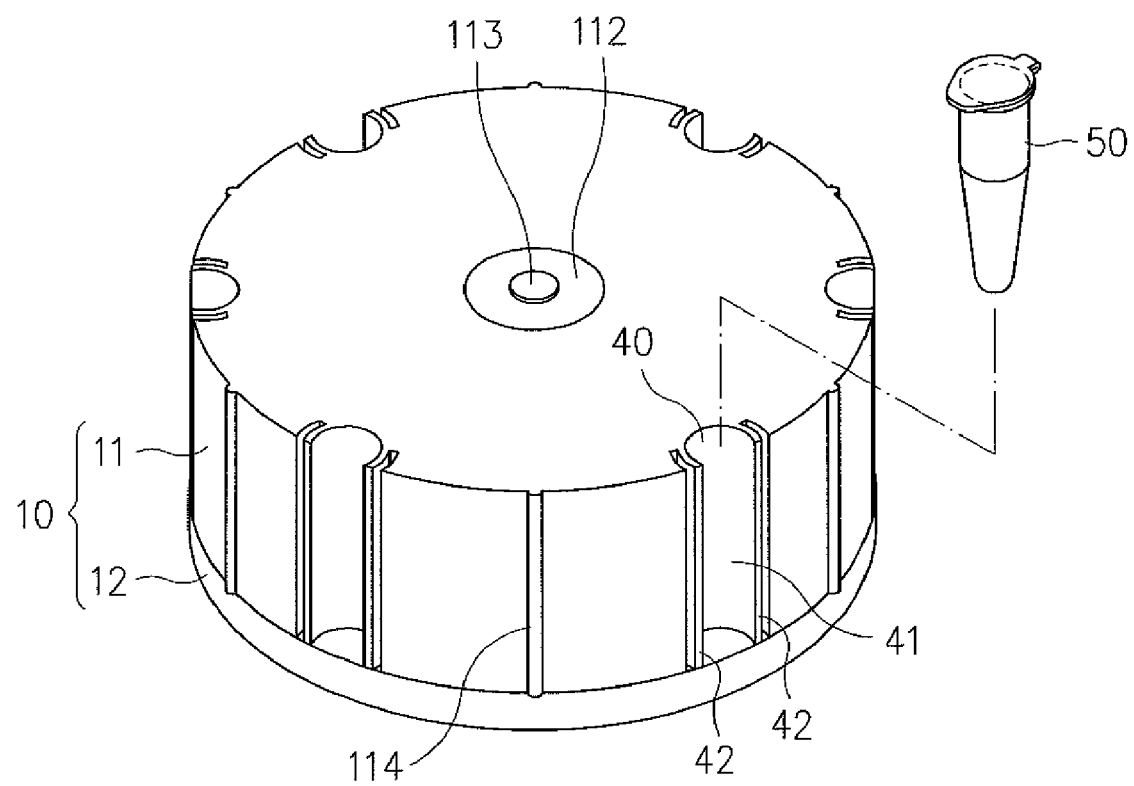
FIG. 2 is a schematic view of a magnetic separation device according to an exemplary embodiment of the invention.
Figure 3:
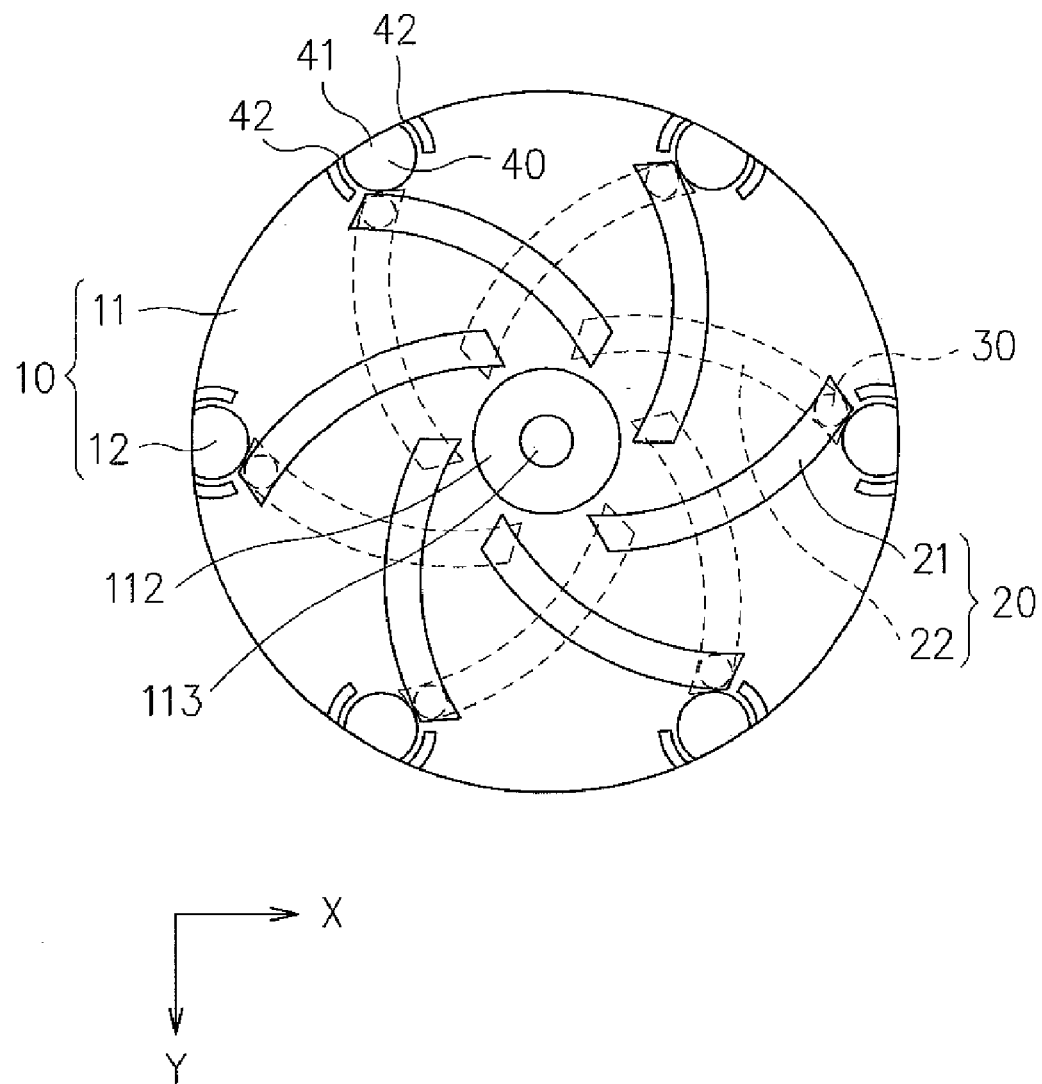
FIG. 3 is a top view of a magnetic separation device according to an exemplary embodiment of the invention.

As shown in FIG. 1 to FIG. 3, a magnetic separation device comprises a separator 10, a plurality of groove sets 20, a plurality of magnetic members 30 as the one illustrated in the figures, and a plurality of test tube slots 40.

The separator 10 includes a top base 11 and a bottom base 12, both shaped like a round disc. As shown in FIG. 1, there is an axial through hole 111 formed at the center of the top base 11 and a pivotal axis 121 disposed at the center of the bottom base 12 that is axially extending into the axial through hole 111 of the top base 11. In addition, the top of the axial through hole 111 formed in the top base 11 is configured with a bearing 112, being riveted by a rivet 113 and thus secured to the top of the pivotal axis 121, thereby, the top base 11 is coupled to the bottom base 12 in a manner that the top base 11 and the bottom base 12 are able to rotate relative to each other centering the pivotal axis 121.

Each of the plural groove sets 20 is composed of an upper groove 21 and a lower groove 22. In the exemplary embodiment shown in FIG. 1 to FIG. 3, there are six groove sets 20, and the upper groove 21 of each groove set is formed on the top base 11 at a surface thereof facing toward the bottom base 12 while the corresponding lower groove 22 is formed on the bottom base 12 at a surface thereof facing toward the top base 11. As shown in FIG. 1, each upper groove 21 is formed at the bottom surface of the top base 11 and is curvedly extending from the pivotal axis 121 toward the outer rim of the top base 11 in a radial and centrifugal manner; and each lower groove 22 is formed at the top surface of the bottom base 12 and is curvedly extending from the pivotal axis 121 toward the outer rim of the bottom base 12 in a radial and centrifugal manner. It is noted that the curvatures of the upper and the lower grooves 21, 22 of the same groove set 20 are opposite to each other.

The magnetic member 30, being a pillar-like permanent magnet, is disposed between the top and the bottom bases 11, 12 in a manner that the two ends of the magnetic member 30 are inset into the upper groove 21 and the lower groove 22 of the same groove set 20 in respective. It is noted that the amount of the magnetic members 30 are dependent upon the amount of groove sets 20. For instance, as there are six groove sets in the embodiment shown in FIG. 1, there should be six magnetic members 30 in correspondence. Moreover, each magnetic member 30 can be an electro magnet or other elements with magnetism.

In addition, each test tube slot 40 is formed at the outer rim of the top base 11 while enabling it axial direction to be parallel to the axial direction of the pivotal axis 121. Similarly, the amount of the test tube slots 40 are also equal to the amount of groove sets 20. For instance, as there are six groove sets in the embodiment shown in FIG. 1, there should be six test tube slots 40 in correspondence. As shown in FIG. 1, each test tube slot 40 is a through hole boring from the top to the bottom of the top base 11 and is formed at the outer rim of the top base 11 as an open slot 41, in which at least a pin clip 42 is arranged at the wall of the open slot 41 for enabling the open slot 41 to open/close with elasticity and holding a test tube, as shown in FIG. 2.

In an exemplary embodiment, the outer wall of the top base 11 is configured with a plurality of bulging bar-like elements 114, by which friction can be provided for allowing a user to grasp the separator 10 or to rotate the top base 11. Moreover, an anti-slip pad 122 is arranged at the bottom base 12 for providing a friction between the separator 10 and the surface where the separator 10 is placed.

Figure 4:
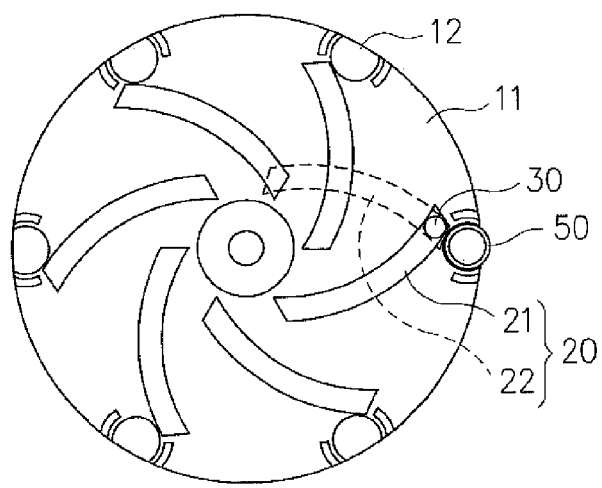
FIG. 4 to FIG. 6 are schematic diagrams showing the proceeding of an operating magnetic separation device of the invention.
Figure 5:
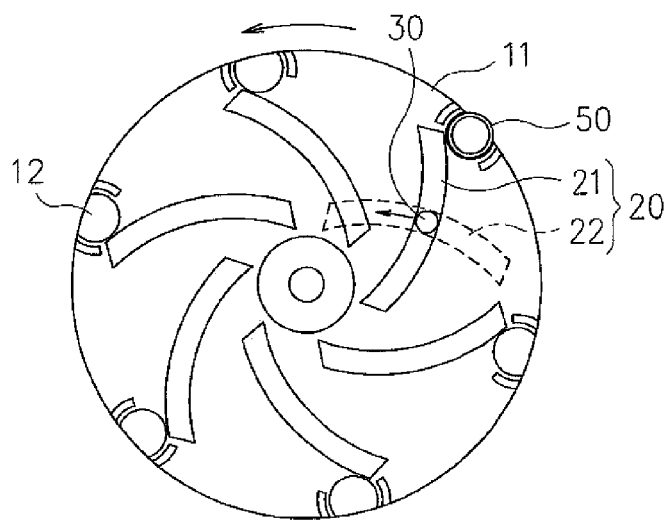
Figure 6:
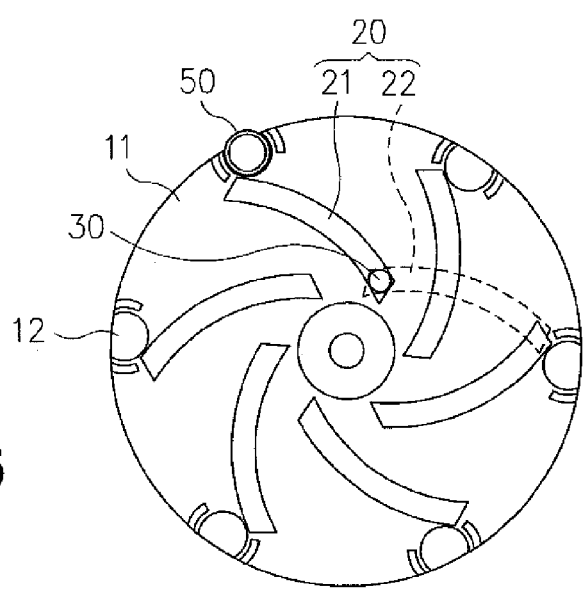

As shown in FIG. 4 to FIG. 6, the operation of the magnetic separation device is illustrated by the use of one groove set 20, one magnetic member 30 and one test tube 50. As shown in FIG. 4, the magnetic member 30 is located at position nearest to the test tube 50 for applying magnetic force on the mixture containing in the test tube 50 as the upper groove 21 and the corresponding lower groove 22 are intersected with each other at their outer ends. In FIG. 5, when the top base 11 is rotated counterclockwisely while simultaneously rotating the bottom base 12 clockwisely, the intersect of the upper groove 21 and the lower groove 22 will move toward the pivotal axis 121 so that the magnetic member is going to slide and move from the outer ends toward the inner ends of the two grooves 21 and 22. As the test tube 50 will be brought to rotate with the rotation of the top base 11 and the top base 21 is kept to rotate counterclockwisely until the upper groove 21 and the corresponding lower groove 22 are intersected with each other at their inner ends, as shown in FIG. 6, the magnetic member 30 is located at position farmost from the test tube 50 and thus no magnetic force will be applied on the mixture of the test tube 50. It is noted that if it is intended to apply magnetic force on the test tube 50, the magnetic member 30 can be driven to slide toward the test tube 50 by driving the top base to rotate clockwisely.

In the exemplary embodiment shown in FIG. 1 to FIG. 3, the upper and the lower grooves 21, 22 are extending parallel to a plane defined by a Cartesian coordinate system of X- and Y-axes whereas the plane is the datum water level. Moreover, as the depths of the extending upper and lower grooves 21, 22 are maintained to be constant, the magnetic member 30 can be moved with two degree-of-freedom capability, that is, the magnetic member 30 will not be raised or descended when it is moving in the upper and lower grooves 21, 22.

Figure 7:
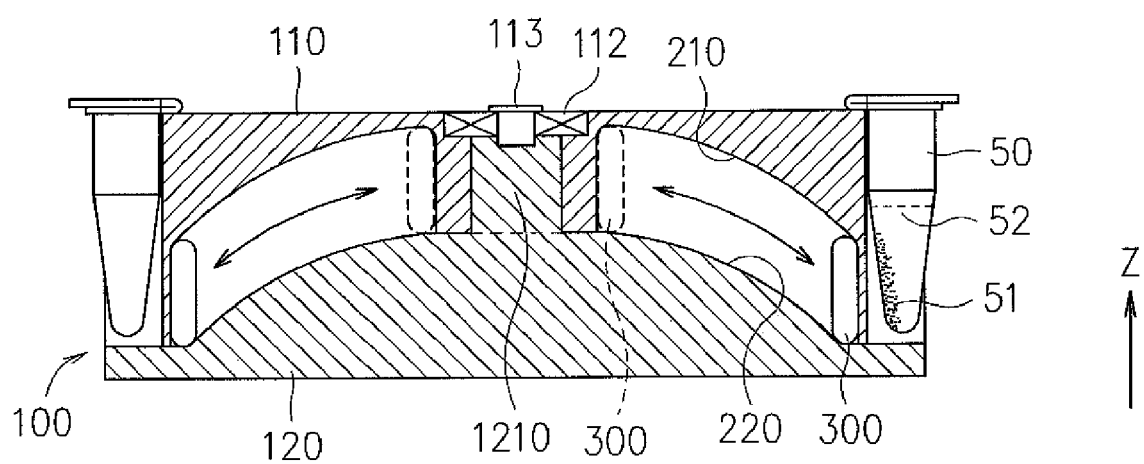
FIG. 7 is an axial cross sectional view of a magnetic separation device according to another exemplary embodiment of the invention.

Please refer to FIG. 7, which is an axial cross sectional view of a magnetic separation device according to another exemplary embodiment of the invention. The separator 100 shown in FIG. 7 includes a top base 110 and a bottom base 120, in which the top and the bottom bases 110, 120 are connected by the use of a pivotal axis 1210, a bearing 112 and a rivet 113 in a manner that the top base 110 and the bottom base 120 are able to rotate relative to each other centering the pivotal axis 1210. Moreover, there are an upper groove 210 formed on the bottom surface of the top base 110 and a lower groove 220 formed on the top surface of the bottom base 120. It is noted that the extensions of the upper and the lower grooves 210, 220 are similar to those described in the embodiment shown in FIG. 3 and thus are not described further herein. However, the embodiment of FIG. 7 is characterized in that: the groove-bottoms of the upper and the lower grooves 210, 220 are curve planes governed by a same curvature while enabling the cross profiles of the two grooves to descend from the pivotal axis 1210 to the outer rim of the separator 100, thereby, there will be a height difference between the magnetic member 300 at the outer ends and the magnetic member 300 at the inner ends. In another word, the upper and the lower grooves 210, 220 are extending in a space defined by a Cartesian coordinate system of X-, Y-, and Z-axes with three degree-of-freedom capability.

When the top base 110 and the bottom base 120 are rotate relative to each other, the magnetic member 300 is driven to move with three degree-of-freedom capability. In FIG. 7, when the magnetic member 300 is driven to move closer to the test tube 50, the magnetic particles 51 containing in the solution of the test tube 50 will be attracted to the side of the test tube 50 that is close to the magnetic member 300 so that liquid phase 52 of the solution can be removed. However, when the rotations of the top and the bottom bases 110, 120 bring the magnetic member 300 to move to the highest location of its moving path governed by the curved upper and lower grooves 210, 220, the magnetic member 300 is located at the position farmost from the test tube 50. Accordingly, by repetitively driving the magnetic member 300 to perform the aforesaid three-dimensional movement for bring the magnetic member 300 to moved toward the test tube 50 and then away from the test tube 50, a wash cycle of a magnetic separation process can be perform repetitively.

It is noted that, other then descending, the cross profiles of the upper and lower grooves 210, 220 can be raised from the pivotal axis 1210 to the outer rim of the separator 100, and thereby, there will still be a height difference between the magnetic member 300 at the outer ends and the magnetic member 300 at the inner ends, but the magnetic member 300 at the outer ends close to the test tube 50 is higher than that at the inner ends. Moreover, the size of the magnetic member 300 is dependent on the magnetic force actually required, and there is no limit regarding to the actual size of the separator 100.

To sum up, the magnetic separation device of the invention is a device capable of utilizing two counter-rotating bases and the groove sets, each composed of two arc-like grooves having curvatures opposite to each other to alter the relative position between a magnet and a sample cell, by which not only a simple magnetic screen effect can be achieved when the magnet is moved away from the sample cell, but also the miniaturization of the whole magnetic separation device is achievable. As the magnetic separation device of the invention is able to alter its magnetic strength applying on a test tube at will at any time according to specific requirements of a magnetic separation process, the washing cycle in the magnetic separation process can be performed without having the test tube to be taken out repetitively, and thereby, the process time can be greatly reduced and also the chances of splashing and cross-contamination are eliminated. In addition, as the rotations of the two bases are reversible, the device is able to apply magnetic force on the test tube again for removing magnetic particles after entities of interest had be eluted.

It is noted that the disc-shaped top bases 11, 110 and bottom bases 12, 120 shown in FIG. 1 and FIG. 7 are only used as illustrations and are not limited thereby. That is, they can be bases of square, polygon, or any other geometrical shapes, only if they can rotate relative to each other centering a pivotal axis and configure with groove set for driving magnetic members to slide therein.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A magnetic separation device, comprising:
   a separator, including a top base and a bottom base;
   at least a groove set, each composed of two arc-shaped grooves having curvatures opposite to each other and arranged in a manner that one of the two arc-shaped groove is formed on the top base at a surface thereof facing toward the bottom base while forming another arc-shaped groove on the bottom base at a surface thereof facing toward the top base;
   at least a magnetic member, being movably fitted inside the two arc-shaped grooves of the at least one groove set; and
   at least a test tube slot, each being formed at the outer rim of a base selected from the group consisting of the top and the bottom base of the separator to be used for fitting a test tube therein;
   wherein the top and the bottom bases are assembled by means of a pivotal axis piercing through about at the center of the top and the bottom bases for enabling the two bases to rotate relative to each other; and
   the magnetic member is driven to slide inside the groove set while the top and the bottom bases are driven to rotate relative to each other, thereby, the magnetic member is moved between two positions whereas one is near the at least one test tube slot and the other is away from the at least one test tube slot.

2. The magnetic separation device of claim 1, wherein the two arc-shaped grooves of the groove set are respectively:
   an upper groove, formed at the bottom surface of the top base and curvedly extending from the pivotal axis toward the outer rim of the top base in a radial and centrifugal manner; and a lower groove, formed at the top surface of the bottom base and curvedly extending from the pivotal axis toward the outer rim of the bottom base in a radial and centrifugal manner;
   whereby the upper groove intersects with the lower groove when the top base and the bottom base are driven to rotate relative to each other.

3. The magnetic separation device of claim 2, wherein the upper and the lower grooves are extending parallel to a plane defined by a Cartesian coordinate system of X- and Y-axes for enabling the magnetic member to move with two degree-of-freedom capability.

4. The magnetic separation device of claim 2, wherein the upper and the lower grooves are extending in a space defined by a Cartesian coordinate system of X-, Y-, and Z-axes for enabling the magnetic member to move with three degree-of-freedom capability.

5. The magnetic separation device of claim 4, wherein the groove-bottoms of the upper and the lower grooves are curve planes governed by a same curvature while enabling the cross profiles of the two grooves to descend from the pivotal axis to the outer rim of the separator.

6. The magnetic separation device of claim 4, wherein the groove-bottoms of the upper and the lower grooves are curve planes governed by a same curvature while enabling the cross profiles of the two grooves to rise from the pivotal axis to the outer rim of the separator.

7. The magnetic separation device of claim 1, wherein both the top base and the bottom base are shaped like a round disc while the centers of the two disc-shaped bases are bored for lodging the pivotal axis.

8. The magnetic separation device of claim 7, wherein an axial through hole is formed at the center of the top base; and the pivotal axis is disposed at the center of the bottom base while axially extending into the axial through hole of the top base for pivotally coupling the top and the bottom bases.

9. The magnetic separation device of claim 8, wherein the top of the axial through hole formed in the top base is configured with a bearing for coupling to the top of the pivotal axis.

10. The magnetic separation device of claim 1, wherein each test tube slot is a through hole boring from the top to the bottom of the base where it is disposed and the axial direction of the through hole is parallel to the axial direction of the pivotal axis.

11. The magnetic separation device of claim 10, wherein the through hole is formed at the outer rim of the base where it is disposed as an open slot, and is configured with at least a pin clip at the wall thereof for enabling the open slot to open/close with elasticity and holding a test tube.

12. The magnetic separation device of claim 1, wherein a plurality of bulging bar-shaped elements are attached to the outer wall of the separator.

13. The magnetic separation device of claim 1, wherein an anti-slip pad is arranged at the bottom of the separator.

14. The magnetic separation device of claim 1, wherein the magnetic member is an element selected from the group consisting of magnets, electromagnets and the combination thereof.

* * * * *